United States Patent [19]

Uhlendorf et al.

[11] 4,269,855
[45] May 26, 1981

[54] (3-ALKYLAMINO-2-HYDROXYPROPOXY)-FURAN-2-CARBOXYLIC ACID ANILIDES AND PHYSIOLOGICALLY TOLERATED ACID ADDITION SALTS THEREOF AND MEDICAMENTS CONTAINING THEM

[75] Inventors: Joachim Uhlendorf, Erftstadt-Lechenich; Hans Betzing, Kerpen-Horrem; Hamied Gabbar, Erftstadt-Lechenich; Erich Graf, Kerpen-Horrem; Ille-Stephanie Doppelfeld, Cologne, all of Fed. Rep. of Germany

[73] Assignee: A. Nattermann & Cie. GmbH, Cologne, Fed. Rep. of Germany

[21] Appl. No.: 155,953

[22] Filed: Jun. 3, 1980

[30] Foreign Application Priority Data

Jun. 12, 1979 [DE] Fed. Rep. of Germany ....... 2923817

[51] Int. Cl.³ .................. C07D 307/54; C07D 307/73
[52] U.S. Cl. ................. 424/285; 260/347.3; 542/406; 542/421
[58] Field of Search .................. 260/347.3; 424/285; 542/406, 421

[56] References Cited

U.S. PATENT DOCUMENTS

| | | | |
|---|---|---|---|
| 3,959,481 | 5/1976 | Davis et al. | 260/347.3 X |
| 4,013,684 | 3/1977 | Merkle et al. | 260/347.3 |
| 4,187,237 | 2/1980 | Deinhammer et al. | 260/347.3 |

*Primary Examiner*—Richard Raymond
*Attorney, Agent, or Firm*—Burns, Doane, Swecker & Mathis

[57] ABSTRACT

(3-Alkylamino-2-hydroxypropoxy)-furan-2-carboxylic acid anilides of the formula:

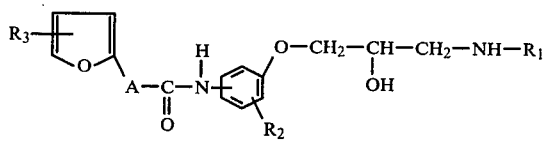

in which $R_1$ denotes a straight or branched $C_1$ to $C_5$ alkyl group or a cyclopropyl or cyclopentyl group, $R_2$ denotes a hydrogen or halogen atom or a methyl, methoxy, nitro or acetyl group, $R_3$ denotes a hydrogen or halogen atom or a nitro group and A denotes a single bond or the —$CH_2$— or —$CH=CH$— group, and physiologically tolerated acid addition salts thereof possess $\beta$-adrenolytic properties and a low toxicity.

5 Claims, No Drawings

(3-ALKYLAMINO-2-HYDROXYPROPOXY)-FURAN-2-CARBOXYLIC ACID ANILIDES AND PHYSIOLOGICALLY TOLERATED ACID ADDITION SALTS THEREOF AND MEDICAMENTS CONTAINING THEM

The present invention provides the (3-alkylamino-2-hydroxypropoxy)-furan-2-carboxylic acid anilides of the formula:

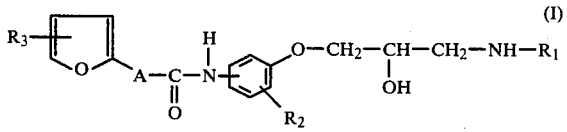

in which $R_1$ denotes a straight or branched chain $C_1$ to $C_5$ alkyl group or a cyclopropyl or cyclopentyl group, $R_2$ denotes a hydrogen or halogen atom or a methyl, methoxy, nitro or acetyl group, $R_3$ denotes a hydrogen or halogen atom or a nitro group, and A denotes a single bond or a —CH₂— or —CH=CH— group, and physiologically tolerated acid addition salts thereof.

These compounds are substituted furancarboxylic acid, furanacetic acid or furanacrylic acid anilide compounds which are valuable as medicaments, since they possess β-adrenolytic properties and a very low toxicity, so that they have an advantageous therapeutic index.

Examples of these new compounds are, inter alia, 2'-(2-hydroxy-tert.-butylaminopropoxy)-furan-2-carboxylic acid anilide, 2'-(hydroxy-tert.-butylaminopropoxy)-furan-2-acetic acid anilide, and 2'-(hydroxy-tert.-butylaminopropoxy)-furan-2-acrylic acid anilide.

The compounds of formula (I) can be prepared by reacting an epoxide of the formula:

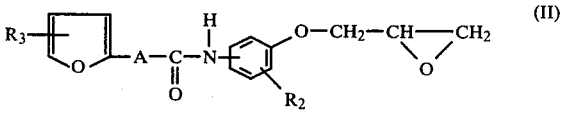

with an alkylamine of the formula H₂N—R₁, the radicals $R_1$, $R_2$ and $R_3$ having in each case the meaning indicated in formula I. The reaction is carried out in the absence or presence of an organic solvent, for example methanol, ethanol or isopropanol, at room temperature or a elevated temperature.

One variant of this method is the condensation of a halogenohydrin of the formula:

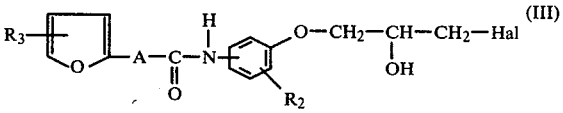

wherein Hal denotes a chlorine, bromine or iodine atom, with an alkylamine of the formula H₂N—R₁. This reaction is carried out in the presence or absence of a solvent, preferably in an autoclave at elevated temperature.

The compounds of formula I can also be obtained by condensing a phenol of the formula:

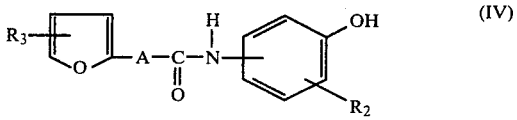

with a compound of the formula X—CH₂—NH—R₁, wherein X is the group

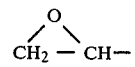

or a group —CHOH—CH—Y in which Y represents a detachable radical, preferably a halogen atom.

The compounds of formula I can also be prepared by reacting an amino derivative of the formula:

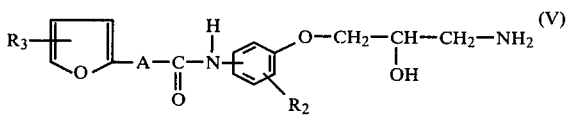

with a compound of the formula Hal-R₁ wherein Hal is a chlorine, bromine or iodine atom or a toluene-p-sulphonyloxy radical. The reaction is appropriately carried out at elevated temperature in the presence of a base, such as, for example, sodium carbonate or potassium carbonate, in a solvent, such as, for example, ethanol or isopropanol.

The compounds of formula I contain an asymmetric carbon atom in the 2-position of the side chain and can, therefore, exist as racemates or as d-isomers or l-isomers. The latter can be obtained in any manner known per se by resolving the racemic product, for example by fractional crystallization of a salt formed with an optically active acid.

The compounds of formula I can be in the form of acid addition salts, which are prepared in the customary manner with inorganic or organic acids. Examples of suitable acids which provide pharmaceutically tolerated salts of the compounds of the invention are hydrochloric acid, sulphuric acid, phosphoric acid, acetic acid, lactic acid, maleic acid or fumaric acid.

The compounds of the invention and their physiologically tolerated acid addition salts exhibit valuable therapeutic properties, especially β-adrenolytic properties, and can, therefore, be employed in human medicine, for example for treatment or prophylaxis of disorders of the coronary vessels and for the treatment of cardiac arrhythmias, especially tachycardia. The compounds of the invention cause a reduction of blood pressure which begins surprisingly rapidly and lasts for a long period, which is also of therapeutic interest. Compared with known β-receptor blocking agents, for example the commercial product 1-isopropylamino-3-(1-naphthyloxy)-propan-2-ol hydrochloride (propranolol hydrochloride), the new compounds have the advantage of reduced toxicity and greater activity. The therapeutic advantage of β-receptor blockers consists, inter alia, in the fact that they are capable of inhibiting the undesirable adrenergic stimuli of the sympathetic nervous system, especially on myocardial β-receptors. Both in animal experiments and in clinical pharmacology, therefore, the reduction in the effects of isoprenalin, a known β-adrenergic antagonist, is made use of as a measure of the effectiveness of such compounds. In this procedure, both the chronotropic action (increasing the frequency) and the inotropic action (increasing the contractile force) of isoprenalin on the action of the heart are determined.

The pharmacological properties of the compounds of the invention were investigated by the following methods:

Experiment 1

For testing in vitro, the left and right auricles of guinea pigs (Pirbright White) were prepared by the experimental procedure of Holtz and Westermann (Naunyn Schmiedeberg's Archiv. Exp. Path. Pharmakol. 225 (1955) 421) and of Wagner and collaborators (Arzneimittel-Forschung 22 (1972) 1061), and their contractile force and their beat frequency were recorded. The concentrations of the compounds of the invention which reduced the isoprenalin effect ($3.2 \times 10^{-8}$ molar for left auricles and $5.8 \times 10^{-9}$ molar for right auricles) to one half were determined as $ED_{50}$ values (probit analysis). The results for one compound of the invention and two reference compounds are listed in the Table below.

Experiment 2

The ventricular pressure of mongrel dogs, anesthetized with chloralose-urethane, was determined, together with other circulation parameters, with the aid of a Millar tip catheter (type PC 350 A, Millar Instruments, Houston, Tex.) introduced into the left heart ventricle, and the maximum rate of pressure increase ($dp/dt_{max}$) was determined by differentiation (HSE operational amplifier, Hugstetten). This rate serves as a measure of the contractile force. The dosage of the compounds of the invention which is capable of reducing to one half the contractile force-increasing action of 0.5 μg/kg of isoprenalin, administered intravenously, was determined graphically in the experiments, using intravenous or intraduodenal administration. The results for one compound of the invention and two reference compounds are shown in the Table below.

Experiment 3

The acute toxicity was determined on NMRI mice by intravenous or oral administration of increasing doses of the compounds of the invention. The death rates were determined within the 7-day follow-up period and the average lethal dose was determined by probit analysis.

The results listed in the Table below show that the compound of the invention has a strong β-receptor blocking action both on isolated organs and on the whole animal and thus provide a therapeutically useful protection against a pathologically increased sympathicotonia. Comparison with two known reference substances used for this purpose shows the advantageous action of the compound of the invention. Propranolol hydrochloride is the most important and most frequently used medicament for this purpose. Special mention should be made of the good action of the compound of Example 1 when administered intraduodenally; this is representative, in general, of enteral administration. Both reference compounds are surpassed in this respect by the said new compound. Compared with the compounds already known, its toxicity is very favorable, so that a value which is 1.5-3 times as high results on calculating the quotient from the values from toxicity ($LD_{50}$) and the effectiveness ($ED_{50}$) as a measure of the "therapeutic range." This shows the outstanding suitability as a therapeutic agent of the compound of the invention. Compared with the reference compounds, the compounds of Examples 3-7 also exhibit an advantageous pharmacological activity similar to that of the compound of Example 1.

TABLE
PHARMACOLOGICAL INVESTIGATION

| Experiment | Administration | Propranolol Hydrochloride | Practolol Hydrochloride | Compound of Example 1 (hydrochloride) |
|---|---|---|---|---|
| 1. Isolated guinea pig auricle | | $ED_{50}$[1] | $ED_{50}$[1] | $ED_{50}$[1] |
| 1.1 Inhibition of increase in contractile force induced by isoprenaline | Bath | $4.5 \times 10^{-7}$ molar | $2.3 \times 10^{-6}$ molar | $2.9 \times 10^{-7}$ molar |
| 1.2 Inhibition of increase in pulse rate induced by isoprenalin | Bath | $1.5 \times 10^{-7}$ molar | $7.1 \times 10^{-7}$ molar | $9.8 \times 10^{-8}$ molar |
| 2. Anaesthetised dogs | | $ED_{50}$[2] | $ED_{50}$[2] | $ED_{50}$[2] |
| 2.1 Inhibition of increase in contractile force induced by isoprenalin | Intravenous | 0.018 mg/kg | 0.2 mg/kg | 0.025 mg/kg |
| 2.2 Inhibition of increase in contractile force induced by isoprenalin | Intraduodenal | 0.2 mg/kg | 0.9 mg/kg | 0.11 mg/kg |
| 3. Acute toxicity | | $LD_{50}$[1] | $LD_{50}$[1] | $LD_{50}$[1] |
| 3.1 Mice | Intravenous | 40 mg/kg | 148 mg/kg | 55 mg/kg |
| 3.2 Mice | Oral | 280 mg/kg | 2,874 mg/kg | 502 mg/kg |
| 4. "Therapeutic range" quotient of 3.2/2.2 | | 1,400 | 3,193 | 4,564 |

[1] determined by means of probit analysis
[2] determined graphically

The invention includes within its scope pharmaceutical compositions comprising one or more compounds of formula I as free base or physiologically tolerated acid addition salt thereof, in association with a customary pharmaceutical auxiliary. Such compositions may be, for example, in the form of tablets, dragees, solutions, emulsions, powders, capsules or depot forms. The compounds of the invention can be administered orally or parenterally. Tablets may be obtained, for example, by mixing the active compound with known auxiliaries, for example inert diluents, such as calcium carbonate, calcium phosphate or lactose, disintegrants, such as maize starch or alginic acid, binders, such as starch or gelatine, lubricants, such as magnesium stearate or talc, and agents for achieving a depot effect, carboxypolymethylene, carboxymethylcellulose, cellulose acetate-phthalate or polyvinyl acetate.

The following Examples illustrate the invention.

EXAMPLE 1

A mixture of 23 g of 2'-(2,3-epoxypropoxy)-furan-2-carboxylic acid anilide, 7.3 g of tert.-butylamine and 50 ml of isopropanol is boiled under reflux for 10 hours. On cooling, 2'-(2-hydroxy-3-tert.-butylaminopropoxy)-furan-2-carboxylic acid anilide crystallizes out from the solution. The chromatographically pure base is obtained in the form of a white solid of melting point 112°–113° C. by recrystallization from ethyl acetate. The yield is 12 g. The colorless, crystalline base is dissolved in alcohol, alcoholic HCl is added and the hydrochloride is induced to crystallize by adding ether dropwise. After isolation, the salt is recrystallized again from ethanol. This gives 10 g of the hydrochloride, melting point 189°–91° C.

The 2'-(2,3-epoxypropoxy)-furan-2-carboxylic acid anilide used as starting material is prepared as follows: 120 ml of 1 N NaOH are added dropwise, at room temperature and in the course of 5 hours, to a suspension of 20.3 g (0.1 mol) of 2'-hydroxyfuran-2-carboxylic acid anilide and 27.8 g (0.3 mol) of epichlorohydrin. The mixture is then stirred for 10 hours and is extracted twice with 50 ml of ether. The combined ether extracts are washed with water, dried over sodium sulphate and concentrated under reduced pressure. The 2'-(2,3-epoxypropoxy)-furan-2-carboxylic acid anilide crystallizes out from the ether. 23 g of the compound, melting at 77°–80° C. are obtained.

EXAMPLE 2

A mixture of 29 g (0.1 mol) of 2'-(3-chloro-2-hydroxypropoxy)-furan-2-carboxylic acid anilide, 30 g (0.4 mol) of tert.-butylamine and 50 ml of isopropanol is heated at 100° C. in an autoclave for 10 hours. Excess amine and solvent are then distilled off under reduced pressure and the residue is taken up in 1 N HCl. After the mixture has been filtered, sodium hydroxide solution is added. The precipitate which has formed is filtered off, washed with water, dried in vacuo and recrystallized from ethyl acetate. 12 g of 2'-(2-hydroxy-3-tert.-butylaminopropoxy)-furan-2-carboxylic acid anilide are obtained. The mixed melting point of the compound with the crystals obtained in accordance with Example 1 shows no depression.

EXAMPLE 3

A mixture of 19.5 g of 4'-(2,3-epoxypropoxy)-3'-acetylfuran-2-carboxylic acid anilide, 12 g of isopropylamine and 30 ml of isopropanol is boiled under reflux for 15 hours. The excess amine and isopropanol are distilled off under vacuum, the residue is taken up in 150 ml of 2 N HCl and extracted by shaking twice with 50 ml of ethyl acetate. The aqueous, hydrochloric acid phase is rendered alkaline with sodium hydroxide solution and is extracted with ethyl acetate again. The ethyl acetate phase is washed with water, dried and evaporated to dryness. The base is recrystallized from acetone. This gives 10.5 g of 4'-(2-hydroxy-3-isopropylaminopropoxy)-3'-acetyl-furan-2-carboxylic acid anilide with a melting point of 135°–138° C. The hydrochloride of this compound was prepared as defined in Example 1. After recrystallization from ethanol, 8.4 g of the hydrochloride, with a melting point of 187°–188° C., are obtained.

The 4'-(2,3-epoxypropoxy)-3'-acetyl-furan-2-carboxylic acid anilide used as starting material is prepared as follows: 150 ml of 1 N NaOH are added dropwise, at room temperature and in the course of 3 hours, to a mixture of 23.7 g (0.1 mol) of (4'-hydroxy-3'-acetyl)-furan-2-carboxylic acid anilide and 27.8 g (0.3 mol) of epichlorohydrin. After 15 hours, the mixture is extracted twice with 50 ml of chloroform. The combined chloroform phases are washed, dried over sodium sulphate and concentrated in vacuo. The residue obtained is 19.5 g of 4'-(2,3-epoxypropoxy)-3'-acetyl-furan-2-carboxylic acid anilide, with a melting point of 105°–107° C.

The (4'-hydroxy-3'-acetyl)-furan-2-carboxylic acid anilide is obtained as follows: 92 g (0.68 mol) of anhydrous aluminum chloride are added in portions to 43.4 g (0.2 mol) of 4'-methoxy-furan-2-carboxylic acid anilide, 46 g (0.58 mol) of acetyl chloride and 150 ml of carbon disulphide. The mixture is heated at 90° C. (bath temperature) for 3 hours. After cooling, 300 ml of water are added dropwise, while cooling with ice. The aqueous solution is shaken twice with 200 ml of chloroform. The chloroform phase is stirred with 2 N NaOH and the phenol is precipitated by acidifying the aqueous phase with concentrated hydrochloric acid. The solid which has been precipitated is filtered off, washed with water and dried. It is recrystallized from ethyl acetate to give 36 g of (4'-hydroxy-3'-acetyl)-furan-2-carboxylic acid anilide with a melting point of 139°–141° C.

EXAMPLE 4

16 g (0.07 mol) of 2'-hydroxy-α-furyl-2-acrylic acid anilide are dissolved in 210 ml of 1 N NaOH at room temperature and 14 g (0.07 mol) of 1-chloro-2-hydroxy-3-tert.-butylaminopropane hydrochloride are added. The mixture is stirred at room temperature for 30 hours and the precipitate which has formed is filtered off, washed with water and dried. The resulting 2'-(2-hydroxy-3-tert.-butylaminopropoxy)-α-furyl-2-acrylic acid anilide is recrystallized from ethyl acetate. Yield: 19 g, melting point 101°–102° C. The hydrochloride, prepared as in Example 1, melts at 126°–129° C. The 2'-hydroxy-α-furyl-2-acrylic acid anilide used as starting material is obtained by reacting p-nitrophenyl α-furyl-2-acrylate with o-aminophenol in dioxane.

EXAMPLE 5

A mixture of 26 g of 5'-chloro-2'-(3-chloro-2-hydroxypropoxy)-furan-2-carboxylic acid anilide, 15 g of tert.-butylamine and 100 ml of isopropanol is boiled under reflux for 40 hours. The mixture is then concentrated to dryness. The residue is taken up in dilute HCl and the neutral substances are extracted by shaking with ethyl acetate. The aqueous phase is rendered alkaline with dilute sodium hydroxide solution and extracted twice with 50 ml of chloroform. The combined chloroform extracts are washed with water, dried with sodium sulphate and concentrated in vacuo. The brownish oil is dissolved in isopropanol and the hydrochloride is precipitated with ethereal hydrogen chloride. This gives 5′-chloro-2′-(3-tert.-butylamino-2-hydroxy-propoxy)-furan-2-carboxylic acid anilide hydrochloride. 10.3 g of the compound, with a melting point of 212°–213° C., are obtained after recrystallizing the compound from ethanol.

The 5′-chloro-2′-(3-chloro-2-hydroxypropoxy)-furan-2-carboxylic acid anilide used as starting material is prepared as follows: 120 ml of 1 N NaOH are added dropwise, at room temperature and in the course of 3 hours, to 23.7 g (0.1 mol) of 5′-chloro-2′-hydroxy-furan-2-carboxylic acid anilide and 27.8 g (0.3 mol) of epichlorohydrin. The mixture is stirred for 12 hours and the precipitate which has formed is filtered off, washed and dried. This gives 26 g of 5′-chloro-2′-(3-chloro-2-hydroxypropoxy)-furan-2-carboxylic acid anilide, with a melting point of 150°–153° C.

The 5′-chloro-2′-hydroxy-furan-2-carboxylic acid anilide is obtained by reacting furan-2-carboxylic acid chloride with an equimolar quantity of 5′-chloro-2′-hydroxyaniline in chloroform.

EXAMPLE 6

A mixture of 14 g of 2′-(2,3-epoxypropoxy)-furan-2-acetic acid anilide, 7.2 g of tert.-butylamine and 30 ml of isopropanol is heated under reflux for 12 hours. The residue obtained after evaporation in vacuo is partitioned between 1 N hydrochloric acid and 50 ml of ethyl acetate. The aqueous phase is rendered alkaline with 1 N sodium hydroxide solution and extracted twice with 50 ml of chloroform. The combined chloroform extracts are concentrated to dryness. The residue is purified by chromatography on a silica gel column. The main fraction, which is eluted with chloroform containing 15% methanol, gives 6.5 g of pure 2′-(hydroxy-3-tert.-butylaminopropoxy)-furan-2-acetic acid anilide.

The hydrochloride is prepared as in Example 1. 2.6 g of the compound, with a melting point of 129°–131° C., are obtained.

The 2′-(2,3-epoxypropoxy)-furan-2-acetic acid anilide used as starting material is prepared as in Example 5 from 2′-hydroxy-furan-2-acetic acid anilide.

EXAMPLE 7

The following compounds have been prepared using the methods Examples 1-6, from the corresponding starting materials:

| | Melting Point of the hydrochloride and recrystallization solvent |
|---|---|
| (a) 2′-(3-Isopropylamino-2-hydroxy-propoxy)-furan-2-carboxylic acid anilide | 194–196° C. (methanol) |
| (b) 2′-(3-sec.-Butylamino-2-hydroxy-propoxy)-furan-2-carboxylic acid anilide | 165–166° C. (ethanol) |
| (c) 2′-(3-Cyclopentylamino-2-hydroxypropoxy)-furan-2-carboxylic acid anilide | 183–186° C. (ethanol) |
| (d) 2′-(3-Cyclopropylamino-2-hydroxy-propoxy)-furan-2-carboxylic acid anilide | 195–196° C. (ethanol) |
| (e) 4′-(3-tert.-Butylamino-2-hydroxy-propoxy)-furan-2-carboxylic acid anilide | 210–213° C. (ethanol) |
| (f) 2′-(3-tert.-Butylamino-2-hydroxy-propoxy)-5-bromofuran-2-carboxylic acid anilide | 189–191° C. (ethanol) |

-continued

| | Melting Point of the hydrochloride and recrystallization solvent |
|---|---|
| (g) 2′-(3-tert.-Butylamino-2-hydroxy-propoxy)-5-nitrofuran-2-carboxylic acid anilide | 202–203° C. (ethanol) |
| (h) 3′-Chloro-4′-(3-tert.-butyl-amino-2-hydroxypropoxy)-furan-2-carboxylic acid anilide | 226–229° C. (ethanol) |
| (i) 5′-Methyl-2′-(3-tert.-butyl-amino-2-hydroxypropoxy)-furan-2-carboxylic acid anilide | 117–179° C. (ethanol) |
| (j) 5′-Nitro-2′-(3-isopropylamino-2-hydroxypropoxy)-furan-2-carboxylic acid anilide | 239–241° C. (methanol) |
| (k) 5′-Nitro-2′-(3-tert.-butyl-amino-2-hydroxypropoxy)-furan-2-carboxylic acid anilide | 234–235° C. (acetone) |
| (l) 5′-Methoxy-2′-(3-tert.-butyl-amino-2-hydroxypropoxy)-furan-2-carboxylic acid anilide | 207–208° C. (ethanol) |

EXAMPLE 8

| Formulation Example | |
|---|---|
| 2′-(3-tert.-Butylamino-2-hydroxy-propoxy)-furan-2-carboxylic acid anilide hydrochloride | 40.0 mg |
| Maize starch | 164.0 mg |
| sec.-Calcium phosphate | 240.0 mg |
| Magnesium stearate | 1.0 mg |
| for a tablet weighing | 445.0 mg |

The individual ingredients are vigorously mixed together and the mixture is granulated in a customary manner. The granules are pressed to give tablets weighing 445 mg, each of which contains 40 mg of active compound.

We claim:

1. (3-Alkylamino-2-hydroxypropoxy)-furan-2-carboxylic acid anilides of the formula:

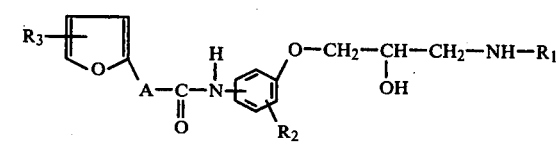

wherein $R_1$ is selected from the group consisting of a straight or branched $C_1$ to $C_5$ alkyl group, cyclopropyl and cyclopentyl; $R_2$ is selected from the group consisting of hydrogen, halogen, methyl, methoxy, nitro and acetyl; $R_3$ is selected from the group consisting of hydrogen, halogen, and nitro; and A is selected from the group consisting of single bond, —$CH_2$—, and —CH=CH—; and physiologically tolerated acid addition salts thereof.

2. 2′-(2-Hydroxy-3-tert-butylaminopropoxy)-furan-2-carboxylic acid anilide and its physiologically tolerated acid addition salts.

3. The hydrochloride salt of a compound as claimed in claim 1.

4. A pharmaceutical composition for the treatment or prophylaxis of disorders of the coronary vessels and cardiac arrhythmias comprising a pharmaceutically effective amount of at least one compound as claimed in claim 1 in association with a pharmaceutical auxiliary.

5. A method for the treatment or prophylaxis of disorders of the coronary vessels and cardiac arrhythmias which comprises administering to a subject an effective amount of a compound as claimed in claim 1.

* * * * *